United States Patent
Kim et al.

(10) Patent No.: US 8,436,223 B2
(45) Date of Patent: May 7, 2013

(54) SEPARATION OF OLEFINS FROM OLEFINS/PARAFFINS MIXED GAS

(75) Inventors: Jong-Nam Kim, Daejeon (KR); Jong-Ho Park, Daejeon (KR); Seong-Jun Lee, Daejeon (KR); Min-Su Ko, Daejeon (KR); Hee Tae Beum, Daejeon (KR); Jongkee Park, Daejeon (KR); Chang Hyun Ko, Daejeon (KR); Sang Sup Han, Daejeon (KR); Soon-Haeng Cho, Daejeon (KR)

(73) Assignees: Korea Institute of Energy Research, Daejeon (KR); SK Energy Co., Ltd, Seoul (KR)

( * ) Notice: Subject to any disclaimer, the term of this patent is extended or adjusted under 35 U.S.C. 154(b) by 815 days.

(21) Appl. No.: 12/593,249

(22) PCT Filed: Mar. 28, 2008

(86) PCT No.: PCT/KR2008/001764
§ 371 (c)(1),
(2), (4) Date: Sep. 25, 2009

(87) PCT Pub. No.: WO2008/120921
PCT Pub. Date: Oct. 9, 2008

(65) Prior Publication Data
US 2010/0048971 A1    Feb. 25, 2010

(30) Foreign Application Priority Data
Mar. 29, 2007 (KR) .................. 10-2007-0030970

(51) Int. Cl.
*C07C 7/12* (2006.01)

(52) U.S. Cl.
USPC ............ 585/809; 585/802; 585/820; 585/822

(58) Field of Classification Search ................... None
See application file for complete search history.

(56) References Cited

U.S. PATENT DOCUMENTS

| | | |
|---|---|---|
| 3,723,561 A | 3/1973 | Priegnitz |
| 3,969,223 A | 7/1976 | Rosback et al. |

(Continued)

FOREIGN PATENT DOCUMENTS

| | | |
|---|---|---|
| EP | 0751106 A1 | 1/1997 |
| EP | 0708070 B1 | 5/1999 |

(Continued)

OTHER PUBLICATIONS

International Search Report for PCT/KR2008/001764, Jul. 2008.

(Continued)

*Primary Examiner* — Tam M Nguyen
(74) *Attorney, Agent, or Firm* — LRK Patent Law Firm

(57) ABSTRACT

The present invention relates to a method for the separation of $C_4$ olefins and $C_4$ paraffins from a $C_4$ hydrocarbon mixed gas including butene-1, trans-2- butene, cis-2-butene, normal butane, isobutane, etc. The method of the present invention produces $C_4$ olefins with high purity by introducing a gaseous $C_4$ mixture into the adsorption tower loaded with adsorbent selectively adsorbing olefins to adsorb $C_4$ olefins and to discharge $C_4$ paraffins to the outlet of the tower, desorbing $C_4$ olefins adsorbed on the adsorption tower with a desorbent $C_5$ hydrocarbon, $C_6$ hydrocarbon, etc.), and then separating the $C_4$ olefin and the desorbent by a distillation process.

14 Claims, 2 Drawing Sheets

| Time | t1 | t2 | t3 | t1 | t2 | t3 | t1 | t2 | t3 |
|---|---|---|---|---|---|---|---|---|---|
| AD-1 | Adsorption | Pressure equalization | Cocurrent depressurization | C4 olefin rinse | Desorption | | | Pressure equalization | Pressurization |
| AD-2 | Desorption | Pressure equalization | Pressurization | Adsorption | Pressure equalization | Cocurrent depressurization | C4 olefin rinse | Desorption | |
| AD-3 | C4 olefin rinse | Desorption | | | Pressure equalization | Pressurization | Adsorption | Pressure equalization | Cocurrent depressurization |

U.S. PATENT DOCUMENTS

| | | | |
|---|---|---|---|
| 4,119,678 A * | 10/1978 | Neuzil et al. | 585/366 |
| 4,362,537 A | 12/1982 | Werner | |
| 4,455,445 A | 6/1984 | Neuzil et al. | |
| 4,718,986 A | 1/1988 | Comiotto et al. | |
| 5,026,482 A * | 6/1991 | Sircar | 210/674 |
| 5,132,485 A | 7/1992 | Ou | |
| 5,365,011 A | 11/1994 | Ramachandran et al. | |
| 6,022,398 A | 2/2000 | Cho et al. | |
| 6,156,950 A * | 12/2000 | Ragil et al. | 585/802 |
| 6,200,366 B1 * | 3/2001 | Bulow et al. | 95/101 |
| 6,984,765 B2 * | 1/2006 | Reyes et al. | 585/639 |

FOREIGN PATENT DOCUMENTS

| | | |
|---|---|---|
| JP | 47-38902 A | 12/1972 |
| JP | 48-62703 A | 9/1973 |
| JP | 54-41803 A | 4/1979 |
| JP | 56-002920 A | 1/1981 |
| JP | 57-197019 A | 12/1982 |
| JP | 61-115033 A | 6/1986 |
| JP | 61-126036 A | 6/1986 |
| JP | 61115033 | 6/1986 |

OTHER PUBLICATIONS

European Search Report for European Patent Application No. 08741021.3 which corresponds to U.S. Appl. No. 12/593,249, filed May 2010.

JPO Office Action for Japanese Patent Application No. 2010-500835 which corresponds to U.S. Appl. No. 12/593,249, filed May 2010.

\* cited by examiner

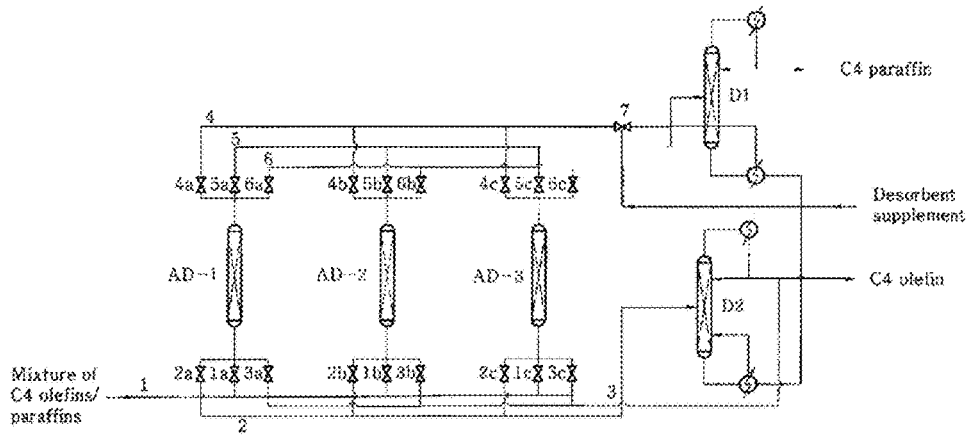

SEPARATION OF OLEFINS FROM OLEFINS/PARAFFINS MIXED GAS

TECHNICAL FIELD

The present invention relates to a method for the separation of C4 olefins (butene-1, trans-2-butene, cis-2-butene, etc.) and C4 paraffins (normal butane, isobutane, etc.) from a C4 hydrocarbon mixed gas including butene-1, trans-2-butene, cis-2-butene, normal butane, isobutane, etc.

BACKGROUND ART

The known method for the separation of C4 olefins (butene-1, trans-2-butene, cis-2-butene, etc.) and C4 paraffins (normal butane, isobutane, etc.) from a C4 hydrocarbon mixed gas including butene-1, trans-2-butene, normal butane, isobutane, etc. involves mainly a distillation process. However, the known method requires the use of distillation towers with a large number of fractionation plates due to the small boiling-point difference of the products to be separated and thus leads to high consumption of energy and to high investment costs.

TABLE 1

Boiling point of the C4 hydrocarbon mixture

| Components | Molecular weight | Boiling point (° C.) |
|---|---|---|
| Isobutane | 58.124 | −11.7 |
| Isobutene | 56.108 | −6.9 |
| Butene-1 | 56.108 | −6.3 |
| 1,3-Butadiene | 54.092 | −4.4 |
| Normal-butane | 58.124 | −0.5 |
| Trans-2-butene | 56.108 | 0.3 |
| Cis-2-butene | 56.108 | 3.7 |

U.S. Pat. No. 4,718,986 (1988) discloses a process for producing butene-1 with a purity of more than 99 wt % from the C4 hydrocarbon mixture of butene-1/isobutane/normal butane/butene-2 by using two distillation towers. According to the above patent invention, the C4 mixture is introduced into the first distillation tower to remove isobutane from the top of the tower. The lower stream from the first distillation tower is introduced into the second distillation tower, obtaining butene-1 with a purity of 99 wt % from the top of the second tower and discharging a mixture of normal butane, butene-2 and butene-1 from the bottom of the second tower. However, since a considerable amount of butene-1 is discharged with the isobutane stream from the top of the first tower and also with the mixture of normal butane, butene-2 and butene-1 from the bottom of the second tower, the above process results in much loss of butene-1. Accordingly, an adsorptive-separation process which can replace the previous distillation process has been studied.

There are a number of known techniques relating to the adsorption-separation processes for a C4 hydrocarbon mixture, for example, a technique for separating butene-1 from a mixture including butene-1/butene-2/isobutylene by using type X or Y zeolite containing potassium ion or barium ion (U.S. Pat. No. 3,723,561, Mar. 27, 1973), a technique for separating butene-1 from a liquid C4 hydrocarbon mixture by using type K-X zeolite (U.S. Pat. No. 4,119,678, Oct. 10, 1978), a technique for separating normal C4 hydrocarbon mixture and isobutylene by using a molecular sieve selective to normal C4 hydrocarbon mixture (U.S. Pat. No. 4,455,445, Jun. 19, 1984), a technique for selectively separating alfa olefin alone from olefins having more than 4 carbon atoms by a liquid adsorption process using a zeolite molecular sieve (U.S. Pat. No. 5,132,485, 1992), a pressure-swing adsorption process for the separation of olefins/paraffins having 2-6 carbon atoms in vapor phase by using type 4A zeolite (U.S. Pat. No. 5,365,011, 1994), and a technique for separating paraffins from a mixture of olefins/paraffins having 2-6 carbon atoms in vapor phase using type X or Y zeolite and regenerating the used adsorbents by using desorbents (EP 0708070 B1, 1999). However, there is no adsorptive separation process that can separate C4 olefins with a purity of more than 95 wt % from a mixture of C4 olefins/paraffins, as can be achieved by the present invention.

DISCLOSURE OF INVENTION

Technical Problem

The existing vapor adsorption separation process for separating a mixture of olefins/paraffins (ex., EP 0708070 B1, 1999) consists of an adsorption step of introducing the mixture of olefins/paraffins into an adsorption tower to adsorb olefins from the mixture and discharge paraffins, and a desorption step of desorbing the ad sorbed olefins by using desorbents.

In the above process, olefins are produced by separation of the mixture of olefins/desorbents resulting from the desorption step via distillation. However, since a small quantity of paraffins is generally adsorbed together with olefins onto olefin selective adsorbents, it is highly difficult to obtain C4 olefins with a high purity of more than 95 wt % by a process consisting only of an adsorption step and a desorption step.

Technical Solution

In order to separate olefins with high purity, the method of the present invention comprises a sequence of adsorption step—olefin rinse step—desorption step. During the olefin rinse step, a portion of high purity C4 olefins resulting from the distillation of olefins/desorbents (desorption agents) is introduced into the adsorption tower where the adsorption step was completed and thus a small quantity of C4 paraffins adsorbed together with C4 olefins is removed from the adsorption tower so that high purity olefin is obtained at the next desorption step.

Advantageous Effects

The present invention achieves an effect that the concentration of olefins in the C4 olefin product increases through the reduction of the concentration of paraffins (ex., isobutane, normal butane, etc.), by introducing a olefin rinse step into a separation process of C4 olefins (butene-1, trans-2-butene, cis-2-butene, etc.) and C4 paraffins (normal butane, isobutane, etc.) from a C4 hydrocarbon mixed gas including butene-1, trans-2-butene, cis-2-butene, normal butane, isobutane, etc.

Now, some embodiments of the present invention are illustrated with reference to the drawings accompanied. However, it is understood that the illustrated embodiments of the present invention are intended to be examples only and the invention is not limited to any embodiments.

BRIEF DESCRIPTION OF THE DRAWINGS

FIG. 1 is a schematic view of the apparatus of obtaining high purity olefins from a mixture gas of C4 olefins/paraffins according to the present invention. The apparatus of the present invention comprises three adsorption towers (AD-1, AD-2 and AD-3) for separating C4 olefins via selective adsorption and two distillation towers (D1 and D2) for separating C4 olefins/desorbents and C4 paraffins/desorbents respectively.

FIG. 2 is a table showing a cycle sequence of the process consisting of seven steps.

FIG. 3 is a table showing a cycle sequence of the process composed of four steps.

FIG. 4 is a table showing a cycle sequence of the process composed of three steps

BEST MODE FOR CARRYING OUT THE INVENTION

Figure 5:
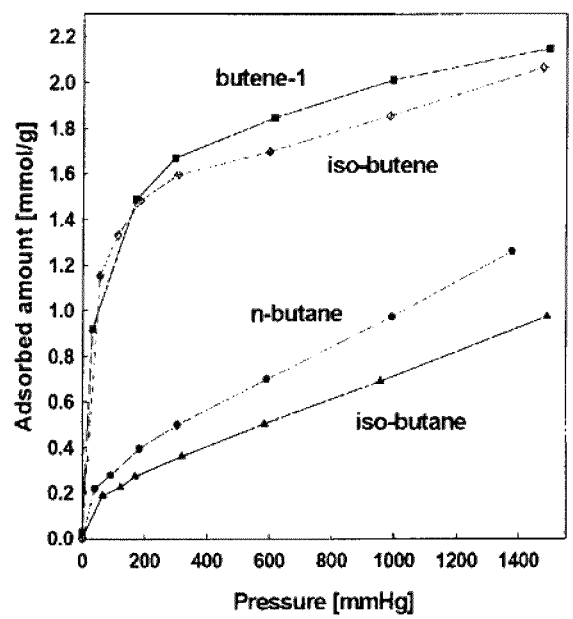
FIG. 5 is a graph of equilibrium adsorption isotherms of olefin-selective adsorbents, i.e., π-complex adsorbents.

The object of the present invention is to provide a method of separating olefins in high yield and purity from a mixture gas of C4 olefins/paraffins, with a reduced consumption of energy, and an apparatus for practicing the method.

The present invention provides a method for separating C4 olefins from a mixture gas composed of C4 olefins/paraffins by performing an adsorption separation process composed of repeated sequential adsorption, olefin rinse and desorption steps in such a way of performing displacement desorption with desorbents, in an apparatus composed of several adsorption towers loaded with adsorbents which adsorb olefins selectively and two distillation towers (one distillation tower for the separation of olefins/desorbents and another distillation tower for the separation of paraffins/desorbents), which comprises the adsorption step for introducing the mixture gas of C4 olefins/paraffins into the adsorption towers loaded with olefin selective adsorbent to adsorb olefins and discharge non-adsorbed paraffins and the desorbents retained in the adsorption tower to the outlet of the adsorption tower;

the C4 olefin rinse step to remove a small amount of paraffins adsorbed together with olefins on the adsorbents by introducing a portion of high purity C4 olefins resulting from the distillation process of olefins/desorbents into the adsorption tower after the completion of the adsorption step and thus increasing the purity of olefins; and the desorption step of obtaining C4 olefins by introducing desorbents into the adsorption towers after the completion of the rinse step, wherein said sequential adsorption, olefin rinse and desorption steps are repeatedly performed, wherein each adsorption towers are operated to perform the different steps with each other at the same time point, and wherein the mixture of olefins/desorbents discharged from the desorption step is introduced into the distillation tower for the separation of olefins/desorbents to obtain high purity olefins by distillation in the distillation tower and the mixture of paraffins/desorbents discharged from the adsorption step is introduced into the distillation tower for the separation of paraffins/desorbents to separating paraffins and desorbents.

Preferably, the method of the present invention further includes a cocurrent depressurization step of discharging the paraffin component residue present in the adsorption towers before the olefin rinse step.

Also preferably, the method of the present invention further includes a pressure equalization step at which the paraffin components present in the interior of the adsorption tower after the completion of the adsorption step is transferred to the another adsorption tower which just completed the desorption step by connecting the two adsorption towers so that the pressure of the adsorption towers becomes equalized, Also preferably, the method of the present invention further includes a cocurrent depressurization step of discharging the paraffin components present in the adsorption towers after the pressure reduction through the pressure equalization step, and a pressurization step which pressurize the adsorption tower to the adsorption pressure by introducing the mixture gas of C4 olefins/paraffins into the adsorption tower partially pressurized through the pressure equalization step.

Also preferably, olefin selective adsorbents for use in the method of the present invention is π-complex adsorbent forming π-complex selectively with olefins, type X zeolite or type Y zeolite, and preferably type 13X zeolite.

Also preferably, the adsorbent for use in the method of the present invention is C5 hydrocarbon or C6 hydrocarbon.

Also preferably, in the method of the present invention, the desorbent separated from the olefin/desorbent distillation tower and the paraffin/desorbent distillation tower is recirculated into adsorption tower.

Also preferably, in the method of the present invention, the operating pressure of the adsorption tower in the C4 olefin/paraffin separation process is 1 to 10 atm (absolute pressure) and the temperature is 20 to 150° C.

The present invention also provides an apparatus for the separation of C4 olefins from a mixture gas of C4 olefins/paraffins, by carrying out repeated sequential adsorption, olefin rinse and desorption steps in such a way of performing displacement desorption with the desorbents to separate C4 olefins from the mixture gas, in three adsorption towers (AD-1, AD-2 and AD-3) loaded with adsorbents which adsorb olefins selectively and two distillation towers (one distillation tower (D2) for the separation of olefins/desorbents and another distillation tower (D1) for the separation of paraffins/desorbents), which comprises the adsorption tower (AD-1) in which the bottom of the tower is connected with the feeding conduit (1) for the mixture gas of C4 olefins/paraffins through the valve (1a), with the C4 olefin/desorbent discharging conduit (2) through the valve (2a) which is connected to the distillation tower (D2), and with the conduit (3) through the valve (3a) which feeds an amount of C4 olefins produced by the distillation tower (D2), and in which the top of the tower is connected with the conduit (4) through the valve (4a) which introduces paraffins and desorbents from the olefin rinse step into the distillation tower (D1), with the conduit (5) through the valve (5a) which feeds paraffins and desorbents discharged from the adsorption step into the distillation tower (D1), and with the conduit (6) through the valve (6a) which feeds the desorbents into the adsorption tower;

the adsorption tower (AD-2) in which the bottom of the tower is connected with the feeding conduit (1) for the mixture gas of C4 olefins/paraffins through the valve (1b), with the C4 olefin/desorbent discharging conduit (2) through the valve (2b) which is connected to the distillation tower (D2), and with the conduit (3) through the valve (3b) which feeds an amount of C4 olefins produced by the distillation tower (D2), and in which the top of the tower is connected with the conduit (4) through the valve (4b) which introduces paraffins and desorbents from the olefin rinse step into the distillation tower (D1), with the conduit (5) through the valve (5b) which feeds paraffins and desorbents discharged from the adsorption step into the distillation tower (D1), and with the conduit (6) through the valve (6b) which feeds the desorbents into the adsorption tower;

the adsorption tower (AD-3) in which the bottom of the tower is connected with the feeding conduit (1) for the mixture gas of C4 olefins/paraffins through the valve (1c), with the C4 olefin/desorbent discharging conduit (2) through the valve (2c) which is connected to the distillation tower (D2), and with the conduit (3) through the valve (3c) which feeds an amount of C4 olefins produced by the distillation tower (D2), and in which the top of the tower is connected with the conduit (4) through the valve (4c) which introduces paraffins and desorbents from the olefin rinse step into the distillation tower (D1), with the conduit (5) through the valve (5c) which feeds paraffins and desorbents discharged from the adsorption step into the distillation tower (D1), and with the conduit (6) through the valve (6c) which feeds the desorbents into the adsorption tower;

the distillation tower (D1) which separates C4 paraffins and desorbents introduced from the adsorption towers (AD-1, AD-2 and AD-3); and the distillation tower (D2) which separates C4 olefins and desorbents introduced from the adsorption towers (AD-1, AD-2 and AD-3).

Preferably, the apparatus of the present invention further includes the valve (7) in the conduit (4) connected to the distillation tower (D1).

MODE FOR THE INVENTION

FIG. 1 is a schematic view of the apparatus of separating C4 olefin from a mixture gas of C4 olefins/paraffins according to the present invention. The apparatus comprises three adsorption towers for separating C4 olefins via selective adsorption and two distillation towers for separating C4 olefins/desorbents and C4 paraffins/desorbents respectively. The basic process of the adsorption tower used in the present invention includes an adsorption step of selectively adsorbing C4 olefins from the gas mixture, a C4 olefin rinse step of removing a small amount of C4 paraffins adsorbed together with C4 olefins; and a C4 olefin desorption step using the desorbents and the process further can includes a pressure equalization step, a cocurrent depressurization step, and a pressurization step. The desorbent discharged from the adsorption step along with olefins or paraffins is separated in the distillation tower and then recycled into the adsorption tower. The preferable desorbents is C5 hydrocarbon or C6 hydrocarbon which has a large difference in boiling point from that of the C4 mixture.

The operating method during a cycle will be explained with reference to FIG. 2 which includes all the processing step.

The mixture gas containing C4 olefins/paraffins is introduced into the adsorption tower (AD-1) loaded with olefin selective adsorbents through the conduit (1) and valve (1a) to adsorb C4 olefins thereon (adsorption step), and the olefin free paraffin stream separated from the mixture is introduced together with the desorbents retained in the adsorption tower before the adsorption step into the distillation tower (D1) through the conduit (5) and the valve (5a) to separate paraffins and desorbents. The adsorption tower (AD-2) carries out the step (desorption step) of desorbing olefin components with the desorbent while the adsorption tower (AD-1) carries out the adsorption step. The desorbents used in the desorption step is obtained from the bottoms of the distillation tower (D1) and the distillation tower (D2) and is introduced into adsorption tower (AD-2) through the conduit (6) and the valve (6b). The olefins discharged with the desorbents is introduced into the distillation tower (D2) through the valve (2a) and the conduit (2) to separate the olefins and the desorbents. The adsorption tower (AD-3) is provided with a portion of the olefins separated from the distillation tower (D2) through the conduit (3) and the valve (3c) to remove a small amount of paraffins adsorbed together with the olefins for the improvement of the purity of olefins (C4 olefin rinse step). At that time, the gas discharged from the adsorption tower (AD-3) is introduced into the distillation tower (D1) through the valve (4c) and the conduit (4).

The adsorption tower (AD-1) at high pressure which just carried out the adsorption step is connected with the adsorption tower (AD-2) at low pressure through the valve (4a) and the conduit (4) and thus a process (pressure equalization step) that allows the pressures of both towers to be in the same pressure is carried out. During the pressure equalization step, the valve (7) is closed. The adsorption tower (AD-3) after the rinse step carries out a desorption step of recovering olefins by introducing the desorbents thereto through the conduit (6) and the valve (6c). The olefins discharged together with the desorbents from the adsorption tower (AD-3) is sent to the distillation tower (D2) through the valve (2c) and the conduit (2) and thus separated from the desorbent.

The adsorption tower (AD-1) after the pressure equalization step is depressurized through the valve (4a) and the conduit (4), and at that time, the discharged gas is introduced into the distillation tower (D1) (cocurrent depressurization step). During the cocurrent depressurization of the adsorption tower (AD-1), a C4 mixture gas is introduced into the adsorption tower (AD-2) through the conduit (1) and the valve (1b) and the adsorption tower (AD-2) carries out a step (pressurization step) of increasing the pressure to the adsorption pressure. At that time, the adsorption tower (AD-3) continues to carry out the desorption step.

The adsorption tower (AD-1) which just finished the cocurrent depressurization step carry out a C4 olefin rinse step, the adsorption tower (AD-2) carries out the adsorption step, and the adsorption tower (AD-3) continues to carry out the desorption step.

In this way, each adsorption tower carry out a sequential adsorption step—pressure equalization step—cocurrent depressurization step—C4 olefin rinse step—desorption step—pressure equalization step—pressurization step continuously.

As shown in FIG. 3 and FIG. 4, the pressure equalization step, the cocurrent depressurization step or the pressurization step can be omitted from the constitution of the process depending on the processing pressure of the adsorption step.

Figure 6:
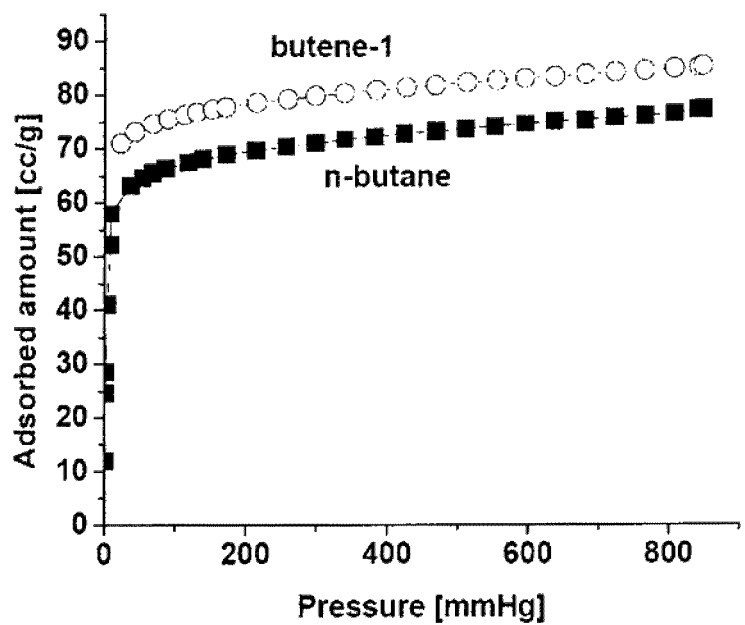
FIG. 6 is a graph of equilibrium adsorption isotherms of olefin-selective adsorbents, i.e., type 13X zeolite adsorbents.

FIG. 5 and FIG. 6 show the adsorption isotherms of the olefin selective adsorbents which can be loaded on the adsorption tower carrying out the method of the present invention. The adsorbents for use in the method of the present invention is π-complex adsorbent forming π-complex selectively with olefins, type X zeolite or type Y zeolite.

Example 1

An experiment for separating olefins from a mixture gas of C4 olefins/paraffins was performed while using type 13X zeolite as an adsorbent for the separation of olefins/paraffins and using C5 mixture gas as a desorbent. The cycle sequence and the apparatus used in this example is shown in FIG. 2 and FIG. 1, respectively. The compositions of the C4 mixture gas and of the C5 mixture gas were shown in table 2. The C4 mixture gas was introduced into the adsorption process at the conditions of 60° C., 2000 mmHg and the flow rate of 1675 ml/min. The C4 olefin rinse step was carried out in the rinse flow rate of 300 ml/min.

TABLE 2

Composition of C4 mixture gas and desorbents

| | Composition (wt %) |
|---|---|
| Components of mixture gas | |
| Iso-butane | 4.73 |
| Normal-butane | 15.3 |
| 1-Butene | 50.0 |
| Trans-2-butene | 19.0 |
| Cis-2-butene | 10.4 |
| Trace components | Remainder |
| Components of desorbents | |
| Normal-pentane | 80.65 |
| Iso-pentane | 18.69 |
| Cyclopentane | 0.56 |
| Trace components | 0.10 |

The performance of the process and the composition of each products resulted from the above process is shown in the following table 3.

TABLE 3

Performance of the process resulted from Example 1

| Flow rate of mixture gas (ml/min) | Flow rate of C4 olefins (ml/min) | Flow rate of C5 desorbents (ml/min) | Product recovered (%) | Composition of products (wt %) | | | | | Purity of olefin |
|---|---|---|---|---|---|---|---|---|---|
| | | | | Isobutane | Normal butane | 1-Butene | Trans-2-butene | Cis-2-butene | |
| 1675 | 300 | 13 | 93.5 | 0.15 | 2.60 | 59.9 | 23.7 | 13.3 | 96.9 |

The result from the experiment carried out with the apparatus as shown in FIG. 1 while omitting the C4 olefin rinse step is shown in the following table 4.

TABLE 4

Performance of the process without the C4 olefin rinse step

| Flow rate of mixture gas (ml/min) | Flow rate of C4 olefins (ml/min) | Flow rate of C5 desorbents (ml/min) | Product recovered (%) | Composition of products (wt %) | | | | | Purity of olefin |
|---|---|---|---|---|---|---|---|---|---|
| | | | | Isobutane | Normal butane | 1-Butene | Trans-2-butene | Cis-2-butene | |
| 2000 | 0 | 10 | 85.16 | 1.87 | 9.30 | 56.3 | 19.7 | 12.2 | 88.2 |

Example 2

Table 5 is a result from the experiment conducted with cycle sequence without the pressure equalization step as shown in FIG. 3.

TABLE 5

Performance of the process of example 2

| Flow rate of mixture gas (ml/min) | Flow rate of C4 olefins (ml/min) | Flow rate of C5 desorbents (ml/min) | Product recovered (%) | Composition of products (wt %) | | | | | Purity of olefin |
|---|---|---|---|---|---|---|---|---|---|
| | | | | Isobutane | Normal butane | 1-Butene | Trans-2-butene | Cis-2-butene | |
| 1610 | 300 | 13 | 93.2 | 0.14 | 2.21 | 60.6 | 23.6 | 12.9 | 97.1 |

Example 3

Table 6 is a result from the experiment performed with the cycle sequence of adsorption step—C4 olefin rinse step—desorption step without the pressure equalization step and the cocurrent depressurization step as shown in FIG. 4.

TABLE 6

Performance of the process of example 3

| Flow rate of mixture gas (ml/min) | Flow rate of C4 olefins (ml/min) | Flow rate of C5 desorbents (ml/min) | Product recovered (%) | Composition of products (wt %) | | | | | Purity of olefin |
|---|---|---|---|---|---|---|---|---|---|
| | | | | Isobutane | Normal butane | 1-Butene | Trans-2-butene | Cis-2-butene | |
| 1640 | 400 | 13 | 91.6 | 0.27 | 2.59 | 23.3 | 61.4 | 12.0 | 96.7 |

INDUSTRIAL APPLICABILITY

The present invention is useful for obtaining the C4 olefins with the high purity of more than 95 wt % by introducing a C4 olefin rinse step to reduce the concentration of C4 paraffins (isobutane, normal butane, etc.) in the C4 olefin product, in the separation of C4 olefins (butene-1, trans-2-butene, cis-2-butene, etc.) and C4 paraffins (normal butane, isobutane, etc.) from a C4 hydrocarbon mixed gas including butene-1, trans-2-butene, cis-2-butene, normal butane, isobutane, etc., as proved in the Examples of the present invention, Although the present invention has been described with respect to the exemplary embodiments in detail, these embodiments are intended only to be illustrative of the present invention and it is apparent to those skilled in the art that a variety of modifications and changes may be made without departing from the spirit and scope of the present invention.

The invention claimed is:

1. A method for separating C4 olefins from a mixture gas of C4 olefins/paraffins by carrying out repeated sequential adsorbing, rinsing, and desorbing in a such way of performing displacement desorption using desorbents, in a separating apparatus of plurality of adsorption towers loaded with adsorbents which selectively adsorb olefins, a distillation tower for the separation of olefins/desorbents and a distillation tower for the separation of paraffins/desorbents, the method comprising:
   adsorbing olefins by introducing the mixture gas of C4 olefins/paraffins into the adsorption towers loaded with adsorbents and discharging non-adsorbed paraffins and the desorbents retained in the adsorption tower at the desorption step to the outlet of the adsorption tower and then discharging them to the distillation towers that separates parrafins and desorbents;
   rinsing with C4 olefin to increase the purity of olefins by introducing a portion of high purity C4 olefins resulting from the distillation process of olefins/desorbents into the adsorption towers after the completion of the adsorption and cleaning a small amount of paraffins adsorbed together with olefins; and
   desorbing C4 olefins by introducing desorbents into the adsorption towers after the completion of the rinsing and discharging the mixture of olefins/desorbents to the distillation towers that separate olefins and desorbents to produce high purity olefins.

2. The method for separating C4 olefins from a mixture gas of C4 olefins/paraffins according to claim 1, wherein the adsorbing, rinsing, and desorbing steps are repeatedly performed at the adsorption towers.

3. The method for separating C4 olefins from a mixture gas of C4 olefins/paraffins according to claim 1, further comprising: cocurrently depressurizing the adsorption towers to discharge the paraffins retained in the adsorption towers before the rinsing.

4. The method for separating C4 olefins from a mixture gas of C4 olefins/paraffins according to claim 1, further comprising:
   pressure equalization step at which the paraffin components present in the interior of the adsorption tower after the completion of the adsorbing step is transferred to the another adsorption tower which just completed the desorption step by connecting the two adsorption towers so that the pressure of the adsorption towers becomes equalized, and further includes a cocurrent depressurization step of discharging the paraffin components present in the adsorption towers after the pressure reduction through the pressure equalization step, and a pressurization step which pressurize the adsorption tower to the adsorption pressure by introducing the mixture gas of C4 olefins/paraffins into the adsorption tower partially pressurized through the pressure equalization step.

5. The method for separating C4 olefins from a mixture gas of C4 olefins/paraffins according to claim 1, wherein the desorbent separated from the olefin/desorbent distillation tower and the paraffin/desorbent distillation tower is recycled into the adsorption tower.

6. The method for separating C4 olefins from a mixture gas of C4 olefins/paraffins according to claim 1, wherein the olefin selective absorbent is selected among the π-complex adsorbent firming π-complex with olefins, type X zeolite or type Y zeolite.

7. The method for separating C4 olefins from a mixture gas of C4 olefins/paraffins according to claim 1, wherein the operating pressure of the adsorption tower is 1 to 10 atm (absolute pressure) and the temperature is 20 to 150° C.

8. The method for separating C4 olefins from a mixture gas of C4 olefins/paraffins according to claim 1, wherein the desorbent is C5 hydrocarbon or C6 hydrocarbon.

9. The method for separating C4 olefins from a mixture gas of C4 olefins/paraffins according to claim 2, further comprising: cocurrently depressurizing the adsorption towers to discharge the paraffins retained in the adsorption towers before the rinsing.

10. The method for separating C4 olefins from a mixture gas of C4 olefins/paraffins according to claim 2, further comprising:
   pressure equalization step at which the paraffin components present in the interior of the adsorption tower after the completion of the adsorbing step is transferred to the another adsorption tower which just completed the desorption step by connecting the two adsorption towers so that the pressure of the adsorption towers becomes equalized, and further includes a cocurrent depressurization step of discharging the paraffin components present in the adsorption towers after the pressure reduction through the pressure equalization step, and a pressurization step which pressurize the adsorption tower to the adsorption pressure by introducing the mixture gas of C4 olefins/paraffins into the adsorption tower partially pressurized through the pressure equalization step.

11. The method for separating C4 olefins from a mixture gas of C4 olefins/paraffins according to claim 2, wherein the desorbent separated from the olefin/desorbent distillation tower and the paraffin/desorbent distillation tower is recycled into the adsorption tower.

12. The method for separating C4 olefins from a mixture gas of C4 olefins/paraffins according to claim 2, wherein the olefin selective absorbent is selected among the $\pi$-complex adsorbent forming $\pi$-complex with olefins, type X zeolite or type Y zeolite.

13. The method for separating C4 olefins from a mixture gas of C4 olefins/paraffins according to claim 2, wherein the operating pressure of the adsorption tower is 1 to 10 atm (absolute pressure) and the temperature is 20 to 150° C.

14. The method for separating C4 olefins from a mixture as of C4 olefins/paraffins according to claim 2, wherein the desorbent is C5 hydrocarbon or C6 hydrocarbon.

\* \* \* \* \*